United States Patent [19]

Ryan

[11] Plant 4,445

[45] Aug. 7, 1979

[54] IMPATIENS PLANT—SENECA

[76] Inventor: John J. Ryan, 39877 Sundale Dr., Fremont, Calif. 94538

[21] Appl. No.: 921,888

[22] Filed: Jul. 3, 1978

[51] Int. Cl.[2] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant, known by the cultivar name SENECA, and discovered by me in commercial greenhouses in Fremont, Calif. SENECA is closest in characteristics to U.S.D.A. ARABESQUE but is particularly characterized by its spreading, yet stiff growth; more open growth habit; its dark variegated foliage; its smaller, yet darker candy-striping on white flowers; and its greater flower numbers.

6 Drawing Figures

BACKGROUND OF THE INVENTION

The present new variety (seedling) was discovered by me in a commercial greenhouse in Fremont, Calif. as a result of the cross pollination of the patented pistil parent 76-13-1 (MAYA) U. S. Plant Pat. No. 4,258 and the unpatented pollen parent 75-1.

Asexual reproduction of my new cultivar by terminal or stem cuttings grown in pots in a plastic (polyethylene) greenhouses in Fremont, Calif. under normal environmental conditions show that the characteristics described come true to form and are established and transmitted through succeeding propagations.

Color readings were taken during daylight hours, in full sun, and all colors are based on the Royal Horticultural Society Colour Chart.

BRIEF SUMMARY

SENECA is closest in characteristics to U.S.D.A. ARABESQUE. The following outstanding characteristics of SENECA distinguish it from U.S.D.A. ARABESQUE:

1. Its spreading, yet stiff growth;
2. Its open growth habit;
3. Its dark, variegated foliage;
4. Its smaller, yet darker candy striping on a white flower; and
5. More floriferous than ARABESQUE.

DESCRIPTION OF THE PHOTOGRAPH

The accompanying colored photograph illustrates the overall appearance of the cultivar SENECA showing the colors as true as reasonably possible for this type of colored reproduction. Under high light the flower color lightens and variegation widens. Most plants give an upright tree form without a pinch, however, the plant in this photograph has a weak lead. The inset photograph illustrates the distinguishing foliage variegation.

DETAILED DESCRIPTION

The following detailed description of SENECA was based on observations made of the new cultivar on Jan. 17, 1978.

I. PLANT

Name: SENECA

Origin: Seedling of cross pollination of patented pistil parent 76-13-1 (MAYA) U.S. Plant Pat. No. 4,258 and unpatented pollen parent 75-1.
Form: Upright, spreading, open.
Height to Flowering: 45 cm.
Growth: Fast.
Type of Cutting: Terminal or stem.
Rooting Time: Typical, 10–14 days.
Rooting Habit: Fast, dendritic.

II. FOLIAGE

Arrangement: Lower leaves of any break opposite (usually just one set); upper foliage of any break whorls of 3 to 5 (more than 5, compressed nodes).
Shape: Elliptical.
Tip: Acuminate.
Base: Attenuate.
Margin: Pectinate.
Veination: Pinnate.
Size: Blade and petiole 8.5 cm. to 13.0 cm.; length of blade 7.0 cm. to 11.0 cm.; width at widest point 2.5 cm. to 4.0 cm.
Surface: Glabrous and glossy.
Variegation: Increases with light and age of break.
Color:

1. *Petiole.*—a. Upper 53 C to 53 D. b. Lower 53 B.
2. *Veins.*—a. Upper 54 D. b. Lower 53 B.
3. *Leaf.*—a. Upper 139 A. b. Lower 181 A.
4. *Variegation.*—

| | | |
|---|---|---|
| a. | Edge 139 A | 20C to 20D |
| b. | Middle | |
| c. | Center | |

III. STEM

Color: 181 A to 181 B.
Internode:

1. *Length.*—Moderate to long.
2. *Size.*—Moderate.

Node expanded (relative to internode): Expanded.
Breaking action: Moderate to good.

IV. FLOWER

Form: Winged petal is narrower than usual leaving open space.

Borne: Typical, on end of branches.

Blooming Habit:

1. *Relative number.*—Average.
2. *Time to flowering.*—Average to long.
3. *Longevity.*—Typical, 3 to 5 days.

Size of Mature Flower: First flower on a plant may be small.

1. *Length.*—5.0 cm. to 6.5 cm.
2. *Width.*—4.5 cm. to 6.0 cm.
3. *Spur.*—6.0 cm. to 7.5 cm.

Color: Candy-striping lightens under high light and heat.

1. *Eye.*—54 A.
2. *Middle.*—56 D (Candy Stripes 52 A).
3. *Edge.*—52 A (at very edge).

Pedicel: 2 D.

V. REPRODUCTIVE ORGANS

Stamen:

| | | |
|---|---|---|
| 1. | Anthers | Typical, fused hood over pistil |
| 2. | Filaments | |

3. *Pollen.*—a. Color: 11 D. b. Abundance: Typical, plenty.

Pistils:

| | | |
|---|---|---|
| 1. | Style | Typical |
| 2. | Ovaries | |

VI. OTHER CHARACTERISTICS:

The form makes a good tree type for a patio plant.

I claim:

1. A new and distinct form of Impatiens plant as described and illustrated, known by the cultivar name SENECA, and particularly characterized by its dark variegated foliage; its smaller, yet darker candy striping of a white flower; its more open growth habit; its spreading, yet stiff growth; and its floriferousness.

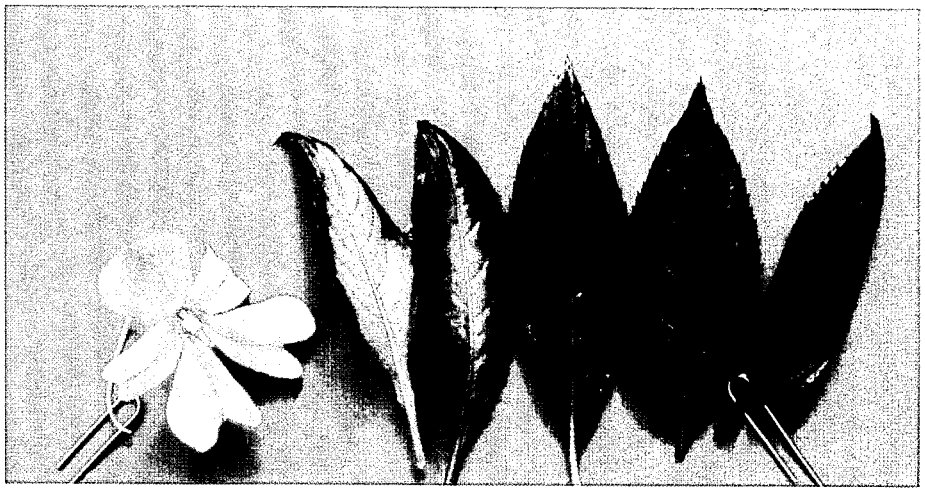

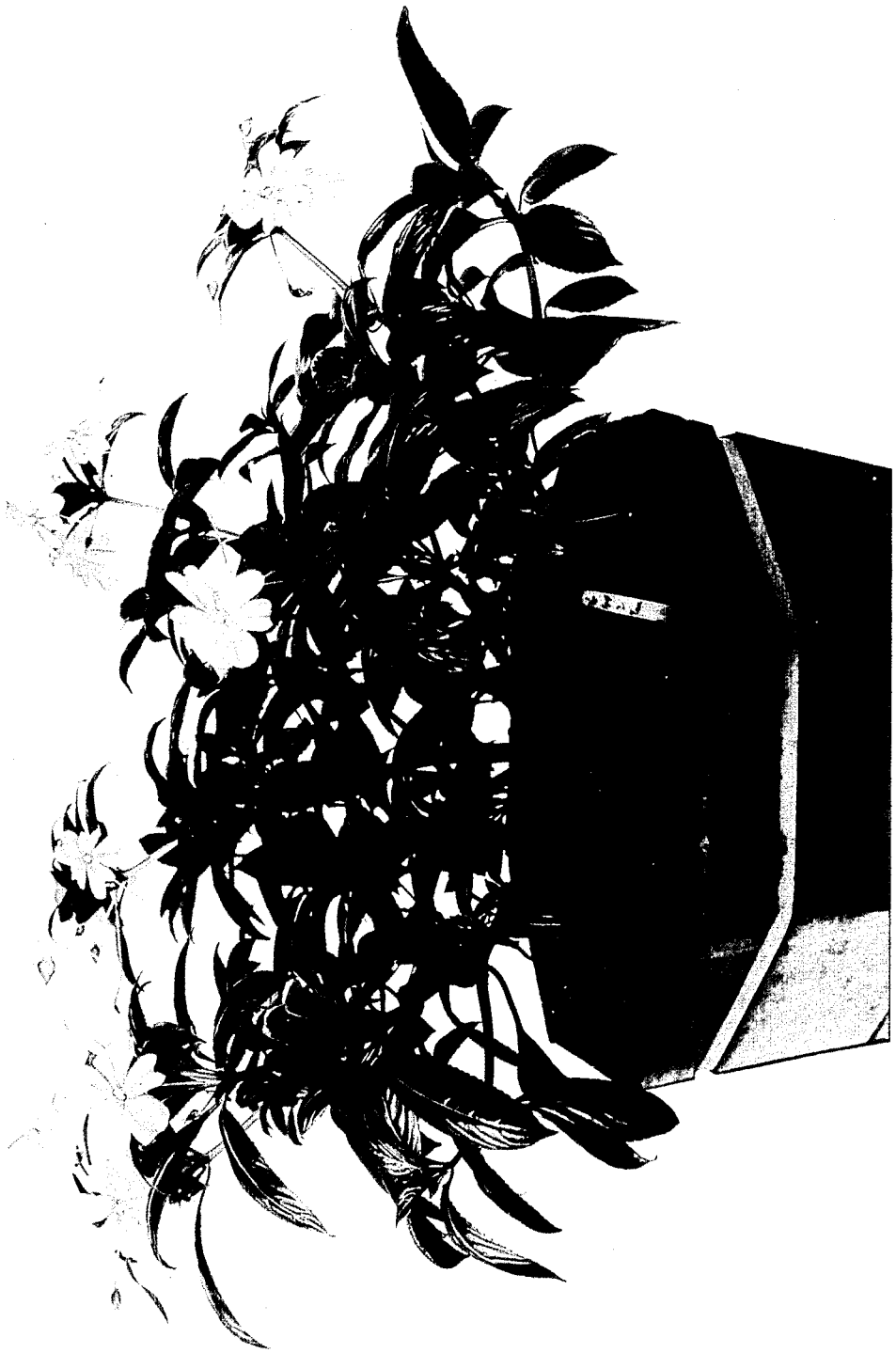

* * * * *